United States Patent [19]

Stahlheber

[11] 4,014,929
[45] Mar. 29, 1977

[54] ETHER CARBOXYLATE MONOHYDRATE
[75] Inventor: Norman Earl Stahlheber, Columbia, Ill.
[73] Assignee: Monsanto Company, St. Louis, Mo.
[22] Filed: Nov. 17, 1975
[21] Appl. No.: 632,347
[52] U.S. Cl. .................... 260/535 P; 252/89 R; 252/132
[51] Int. Cl.² .......................................... C07C 59/23
[58] Field of Search .................................. 260/535
[56] References Cited
UNITED STATES PATENTS

| | | | |
|---|---|---|---|
| 3,821,296 | 6/1974 | Blumbergs | 260/535 P |
| 3,904,684 | 9/1975 | Tsuda et al. | 260/535 P |
| 3,914,297 | 10/1975 | Lamberti et al. | 260/535 P |
| 3,925,465 | 12/1975 | Nara et al. | 260/535 P |

*Primary Examiner*—Paul J. Killos
*Attorney, Agent, or Firm*—N. E. Willis; J. E. Maurer; H. B. Roberts

[57] ABSTRACT

A novel, crystalline, ethercarboxylate monohydrate useful as a detergency builder exhibits excellent handling and thermal stability properties and is particularly suited for use in preparing detergent formulations.

5 Claims, No Drawings

ETHER CARBOXYLATE MONOHYDRATE

BACKGROUND OF THE INVENTION

This invention relates to a novel, crystalline, ether-carboxylate monohydrate particularly suited for processing into detergent formulations and to processes for preparation of such monohydrate. It has been discovered that a compound represented by the formula:

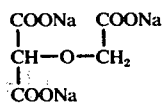

exhibits excellent functionality as a detergency builder. This compound and its use as a detergency builder is described in U.S. Pat. No. 3,865,755, the disclosure of said patent being incorporated herein by reference. Under conditions of high relative humidity, the amorphous form of this compound tends to be hygroscopic and water uptake can result in problems of agglomeration of the compound per se or the detergent formulations in which it is employed. A higher hydrate (tri or tetra) of the compound, which is substantially non-hygroscopic, can be prepared by evaporating a solution of the compound at ambient tempertures. However, the trihydrate loses water of hydration at relatively low temperatures (around 100° C.) and if rapidly dried, as in spray-drying processes for the preparation of detergent formulations, is converted to amorphous form.

It is apparent, therefore, that provision of a form of the above-discussed compound which is relatively non-hygroscopic and thermally stable would constitute an advance in the art.

SUMMARY OF THE INVENTION

It is an object of this invention to provide a relatively non-hygroscopic, thermally stable, crystalline hydrate of the compound:

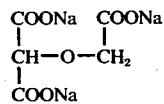

and processes for preparing such crystalline hydrate. The compound of this invention fulfilling these objectives is a crystalline monohydrate represented by the formula:

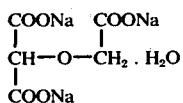

and whose preparation and properties will be understood from the following description of the preferred embodiments.

DESCRIPTION OF THE PREFERRED EMBODIMENTS

The compound of the present invention is a novel crystalline monohydrate represented by the formula:

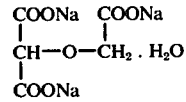

and characterized by an X-ray diffraction pattern exhibiting strong diffraction lines corresponding to approximate values of interplanar spacing d: 8.14 A, 5.65 A, 5.45 A, 5.24 A, 4.50 A, 4.35 A, 3.42 A, 2.77 A, 2.59 A, and 2.38 A. The term "approximate" is used to indicate that the interplanar spacings recited may vary by as much as 1% due to factors such as variations in analytical techniques, co-crystallization of minor amounts of other materials, etc.

This novel crystal hydrate has desirable handling properties generally associated with crystalline materials, and is substantially less hygroscopic than anhydrous crystalline or amorphous forms of the compound. Further, the novel crystalline hydrate of this invention has excellent thermal stability and does not lose water of hydration readily at temperatures below 220° C. as contrasted to the trihydrate which loses water at about 100° C. and the dihydrate which loses water at about 135° C. In addition, the monohydrate is more readily separated from slurries than other hydrates due to its more controllable crystallization characteristics.

The crystalline monohydrate of this invention is prepared by crystallization from an aqueous solution of:

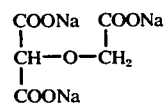

If the

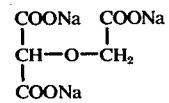

is prepared by neutralization or saponification of acids or esters thereof with sodium hydroxide, care must be taken to ensure that excess sodium hydroxide is neutralized or removed so that the total amount of sodium hydroxide in the solution is less than 5% of the weight of

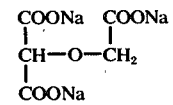

in the solution. Otherwise, unduly large amounts of what appears to be a dihydrate rather than the desired monohydrate will be crystallized from the solution in the process hereinafter described. Neutralization of excess sodium hydroxide to form sodium carbonate can be conveniently accomplished by bubbling carbon dioxide into the solution until the pH is below 11.5.

It is further necessary that crystallization and separation of monohydrate from the solution be effected at temperatures between 50° C. and 220° C., with the use of temperatures near the boiling point (110°–115° C.) being preferred.

Further, heat input to the solution should be controlled to prevent formation of a solution which is more than about 5% super-saturated. If heat input is unduly high (e.g., if the solution is vigorously boiled), excess super-saturation may cause the solution to become highly viscous and, on further heating, lead to the formation of amorphous solids rather than the desired crystalline monohydrate.

The precipitation of the crystalline monohydrate can be promoted by addition of seed crystals of the monohydrate and/or addition of an organic liquid which is miscible with water but which exhibits relatively low solvation of the monohydrate, for example, methanol. The precipitated, crystalline monohydrate can be separated by conventional mechanical procedures, and heating continued to remove any free water or organic solvent.

The practice of the invention is further illustrated by the following Examples wherein all parts and percentages are by weight unless otherwise indicated.

EXAMPLE I

A solution of 1 part

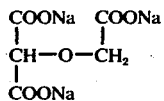

substantially free of sodium hydroxide in 1 part water is formed and admixed with 1 part methanol. The mixture is refluxed at atmospheric pressure for about 2 hours and a crystalline solid precipitate forms which is separated from the heated mixture. This crystalline solid is identified by thermogravimetric and differential thermal analyses as the monohydrate:

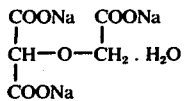

and exhibits an X-ray diffraction pattern characterized by the following interplanar spacings $d$: 8.14 A, 5.65 A, 5.45 A, 5.24 A, 4.50 A, 4.35 A, 3.42 A, 2.77 A, 2.59 A, and 2.38 A.

EXAMPLE II

About 1,000 grams of a 40% aqueous solution of:

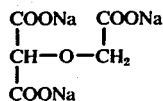

substantially free of sodium hydroxide is heated to boiling. As evaporation of water raises the solids concentration of the solution to 57%, 58½%, 60%, 61½%, 1 gram of monohydrate prepared according to Example I is added as "seed material". Upon the last seeding, the solution becomes and remains turbid. Seeding is discontinued and boiling is continued with heat input being controlled so that the boiling point does not exceed 113° C. (if unduly high heat input were employed a more highly super-saturated solution having a boiling point in excess of 113° C. would be formed). The boiling is continued until a slurry containing substantial amounts of solids are present at which point the solids are separated and identified as the monohydrate:

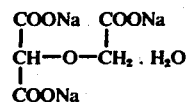

by the procedures set forth in Example I above.

The novel, crystalline monohydrate of the present invention can be employed in detergent formulations as described, for example, in previously referenced United States Patent 3,865,755. The use of the novel, crystalline monohydrate is particularly advantageous for use in preparing detergent formulations by well-understood spray-drying techniques in view of the high thermal stability of the monohydrate.

What is claimed is:

1. A compound represented by the formula:

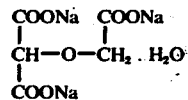

and characterized by an X-ray diffraction pattern exhibiting strong diffraction lines corresponding to the approximate values of interplanar spacing $d$: 8.14 A, 5.65 A, 5.45 A, 5.24 A, 4.50 A, 4.35 A, 3.42 A, 2.77 A, 2.59 A, and 2.38 A.

2. A process for making a compound represented by the formula:

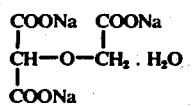

and characterized by an X-ray diffraction pattern exhibiting strong diffraction lines corresponding to the approximate values of interplanar spacing $d$: 8.14 A, 5.65 A, 5.45 A, 5.24 A, 4.50 A, 4.35 A, 3.42 A, 2.77 A, 2.59 A, and 2.38 A, said process comprising forming an aqueous solution of:

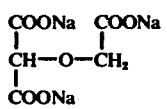

containing less than 5% sodium hydroxide based on the weight of

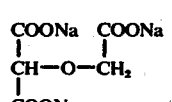

in said solution, and crystallizing and separating

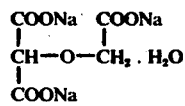

from said solution while maintaining said solution at a temperature between 50° and 220° C., and at less than 5% super-saturation.

3. The process of claim 2 wherein the solution is maintained at its boiling point.

4. The process of claim 2 wherein precipitation of crystalline:

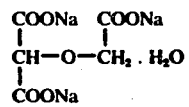

is promoted by contacting said solution with an organic liquid miscible with water and having low solubility for:

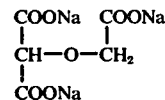

5. The process of claim 2 wherein precipitation of the crystalline:

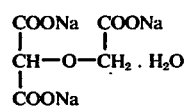

is promoted by seeding said solution with crystalline:

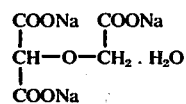

* * * * *